United States Patent [19]
Gergely et al.

[11] Patent Number: 5,869,095
[45] Date of Patent: Feb. 9, 1999

[54] CHEWABLE TABLET WITH AN EFFERVESCENT ACTION

[75] Inventors: Gerhard Gergely, Gartengasse 8, A-1053 Vienna; Irmgard Gergely; Thomas Gergely, both of Vienna, all of Austria

[73] Assignee: Gerhard Gergely, Vienna, Austria

[21] Appl. No.: 913,706

[22] PCT Filed: Jul. 18, 1996

[86] PCT No.: PCT/EP96/03165

§ 371 Date: Sep. 22, 1997

§ 102(e) Date: Sep. 22, 1997

[87] PCT Pub. No.: WO97/04754

PCT Pub. Date: Feb. 13, 1997

[30] Foreign Application Priority Data

Jul. 31, 1995 [CH] Switzerland ............. 2230/95

[51] Int. Cl.$^6$ .................................... A61K 9/46
[52] U.S. Cl. .................... 424/466; 424/441; 424/465; 514/777

[58] Field of Search ................ 424/466, 441, 424/465

[56] References Cited

U.S. PATENT DOCUMENTS 4,650,669  3/1987  Alexander et al. ............. 424/44

FOREIGN PATENT DOCUMENTS

| | | |
|---|---|---|
| A1 0-351353 | 1/1990 | European Pat. Off. . |
| A1 0-415326 | 3/1991 | European Pat. Off. . |
| A1 0-525388 | 5/1993 | European Pat. Off. . |
| WO 91/04757 | 4/1991 | WIPO . |
| WO 91/07174 | 5/1995 | WIPO . |

*Primary Examiner*—Thurman K. Page
*Assistant Examiner*—James M. Spear
*Attorney, Agent, or Firm*—Oliff & Berridge, PLC

[57] ABSTRACT

A chewable tablet or lozenge has an effervescent action and acid particles and/or carbonate particles coated with a hydrocolloid. The chewable tablet or lozenge has a pleasant, fizzy feeling in the mouth during dissolution. The tablet contains a pharmaceutical formulation which can be taken directly orally as a chewable tablet or lozenge.

24 Claims, No Drawings

CHEWABLE TABLET WITH AN EFFERVESCENT ACTION

SUMMARY OF THE INVENTION

This application is a 371 of PCT/EP96/03165 filed Jul. 18, 1996.

The invention relates to a chewable tablet or lozenge with an effervescent action comprising acid and/or carbonate particles of an effervescent base that are coated with a soluble hydrocolloid which is preferably slightly or rapidly soluble. Such tablets have been developed in order to generate a pleasant fizzy feeling in the mouth with the saliva during dissolution. They are described, for example, in EP-A1-525,388 or in WO91/04757.

BACKGROUND OF THE INVENTION

However, the inventors have now set themselves the object of providing a tablet for pharmaceutical formulations which can be both taken directly orally as a chewable tablet or lozenge with a slight effervescent effect and therefore pleasant fizzy feeling in the mouth and dissolved or suspended in (preferably 50–100 ml) of water, in particular in less than 2 min, with effervescence. It is in fact highly desirable to have a tablet which generates a pleasant fizzy feeling on chewing or sucking but which, if required, can be dissolved in a (very small) amount of water if the patient prefers to drink a solution. The tablets mentioned at the outset are however unsuitable for dissolution in water before being taken: the tablet according to EP-A1-525,388 has insufficient effervescent base for this purpose since up to two thirds of the effervescent components have already reacted, i.e. only a single carboxyl group of the citric acid may be free; all tablets according to the examples of WO91/04757 have dissolution times of well over 5 minutes in fresh water.

As the inventors of the present application have surprisingly found, this is due, inter alia, to three aspects of the formulation which had not been taken into account by the inventors of WO91/04757 because they were indeed concerned only with a chewable tablet or lozenge, which, according to the description, was to dissolve in water at 37° C. in less than 10 minutes. The stated relevant lower limit of 30 seconds cannot be achieved with the formulation of WO91/04757.

A first reason for this is the use of a lubricant for tabletting, which is essential according to the description. Even a relatively low content of lubricant makes the individual components hydrophobic and thus contributes very substantially to poorer dissolution behaviour of the tablet in water.

A second reason is the encapsulation or coating of the particles of the active substance: the coating material penetrates into the voids during compression and thus also blocks access to the effervescent particles. The effervescent particles then react much more slowly with the water thus impeding the dissolution of the tablets.

A third reason is the use of relatively large amounts of rapidly soluble substances as fillers, such as, for example, sorbitol alone or as a mixture with a sucrose which is formulated as a tabletting assistant and in turn contains lubricant although only in small amounts.

Surprisingly, it has in fact been found that relatively rapidly soluble fillers in a tablet having a relatively low content of effervescent base (owing to any direct oral intake of the tablet, the effervescent effect must not be too great, otherwise it will be found to be unpleasant) prolong the dissolution time of the tablet. The reason for this is that, on introduction of the tablet into water, the amounts of rapidly soluble fillers, which are large in comparison with the amount of the effervescent base, very rapidly form a locally very highly concentrated solution in which the dissolution and reaction of the effervescent components and hence the disintegration of the tablet take place only slowly.

On the other hand, if the lubricant and/or the encapsulation of the active substance are omitted, an unpleasantly strong effervescent effect may be achieved in the mouth if the tablet is to be chewed or sucked, even with small amounts of effervescent components which are required for the dissolution of the tablet in fresh water.

Attempts to achieve the object described at the outset by means of a disintegrating effervescent material doped with a small amount of effervescent base, for example according to EP-A1-501,985, also failed since the disintegrating agents always left behind a sandy, rough impression during chewing or sucking, which was found to be unpleasant.

The inventors have demonstrated this on the basis of the examples and have solved the stated problems as described herein and in the appended claims such as by formulating a tablet with an effervescent action comprising a pharmaceutically active substance, acid particles, and/or carbonate particles of an effervescent base that are coated with a soluble hydrocolloid that is preferably slightly or rapidly soluble, and/or wherein the pharmaceutical substance is free of encapsulating substances and/or the tablet mixture is free of lubricants. Advantageous further developments and alternatives of the invention are described as described herein and in the appended claims.

The small amounts of water in the saliva, in which indeed other substances are also dissolved, do not dissolve a hydrocolloid coat on the effervescent components so rapidly that an undesirably strong effervescent action would occur. Even small amounts of the hydrocolloid thus slow down the reaction of the effervescent components with one another in the mouth quite dramatically, while the hydrocolloid—in particular an essentially readily soluble one, such as, for example, maltodextrin, polyvinylpyrrolidone or guar gum—dissolves in the water very rapidly and prolongs the dissolution time of the tablet only to an insignificant extent.

DETAILED DESCRIPTION OF PREFERRED EMBODIMENTS

EXAMPLE 1

This Example corresponds to the prior art; Example 1 of WO91/04757 was reworked, with the following variations:
a. Acetaminophen encapsulated, with lubricant (Mg stearate)
b. Acetaminophen encapsulated, without lubricant
c. Acetaminophen unencapsulated, with lubricant (Mg stearate)
d. Acetaminophen unencapsulated, without lubricant
e. Placebo (without active substance), with lubricant (Mg stearate)
f. Placebo (without active substance), without lubricant Four different fillers were alternatively added to these six systems:
a. 400 mg each of Comprizucker® and sorbitol (corresponding exactly to Example 1 of WO91/04757)
b. 800 mg of Comprizucker® alone
c. 800 mg of sorbitol alone
d. 400 mg each of sorbitol and mannitol.

|  | Acetaminophen encapsulated | | Acetaminophen unencapsulated | | Placebo (without active substance) | |
| --- | --- | --- | --- | --- | --- | --- |
|  | a) with Mg stearate | b) without Mg stearate | c) with Mg stearate | d) without Mg stearate | e) with Mg stearate | f) without Mg stearate |
| a) Comprizucker (400 mg) + sorbitol (400 mg) | after 5 min, the tablet has practically not dissolved at all | after 5 min, the tablet has practically not dissolved at all | after 5 min, the tablet is still virtually whole | Dissolution time 140 sec | after 5 min, 3/4 of the tablet has dissolved | Dissolution time 140 sec |
| b) Sorbitol (800 mg) | after 5 min, the tablet has practically not dissolved | after 5 min, the tablet has practically not dissolved | after 5 min, the tablet is still virtually whole | Dissolution time 160 sec | after 5 min, 3/4 of the tablet has dissolved | Dissolution time 170 sec |
| c) Comprizucker (800 mg) | after 5 min, the tablet is still virtually whole | after 5 min, the tablet is still virtually whole | after 5 min, the tablet is still virtually whole | Dissolution time 135 sec | after 5 min, 3/4 of the tablet has dissolved | Dissolution time 100 sec |
| d) Mannitol (400 mg) + sorbitol (400 mg) | after 5 min, the tablet is still virtually whole | after 5 min, the tablet is still virtually whole | after 5 min, 1/2 the tablet has dissolved | Dissolution time 125 sec | after 5 min, the tablet has virtually dissolved | Dissolution time 95 sec |

As is evident from the table, with encapsulated active substance and lubricant, the tablet has in each case practically not dissolved at all or only superficially dissolved 5 minutes after introduction into 100 ml of fresh water.

Even with unencapsulated active substance, but with lubricant, the tablet has practically not dissolved or only half dissolved 5 minutes after introduction into 100 ml of fresh water. Only with unencapsulated active substance and without lubricant is the dissolution time—depending on the filler used—still 135 to 165 sec and only when half the sorbitol is replaced by mannitol is it then 120 sec.

However, even the placebo variant shows how troublesome the proposed fillers Comprizucker® and sorbitol are. In summary, both the active substance encapsulation and the lubricant have a disadvantageous effect on the dissolution behaviour; moreover, replacing the Comprizucker® by mannitol is sufficient to have a positive effect, and dissolution times as long as 2 minutes are achieved, which however is still too high for practice.

EXAMPLE 2

An effervescent base is first prepared as follows: 86 parts of citric acid powder, 8.3 parts of malic acid, 95 parts of sodium bicarbonate, 13.8 parts of sodium carbonate <0.1 mm, 5.5 parts of sodium cyclamate, 1.1 parts of saccharin sodium and 0.3 part of aspartame are mixed in a vacuum vessel heated to 60° C. In addition, a solution of 60 parts of maltodextrin, 12 parts of trisodium citrate dihydrate in 27 parts of water is prepared. 4.5 parts of this solution (corresponding to 1.3 parts of maltodextrin, relative to effervescent base—the coating results in citric acid not being found so acidic during sucking but the tablet dissolving sufficiently rapidly) are sprayed in 5 cycles onto the powder mixture in the vacuum vessel and distributed uniformly with vibratory mixing, granulation taking place at the same time. After each cycle, drying is carried out in vacuo and the material is then discharged through a 2 mm sieve. Expediently, another 5 parts by weight of maltodextrin are applied to the resulting granules after the final cycle and prior to drying and are distributed uniformly with stirring and—preferably in vacuo—dried with slow stirring.

180 parts of the effervescent base thus prepared are mixed with 720 parts of mannitol, 100 parts of acetylsalicylic acid <0.3 mm and 0.3 part of docusate sodium aerosol OTB powder and 0.5 part of polyvinylpyrrolidone K25, 3.0 parts of vanilla flavour and 0.3 part of menthol and the mixture is compressed to give tablets of 1 gram each. On direct oral intake, the tablets produce a pleasant fizzy feeling in the mouth or dissolve in 100 ml of water at 15°–20° C. in 55 seconds.

The maltodextrin can also be replaced by another hydrocolloid, such as, for example, polyvinylpyrrolidone, guar gum or dextrin (the latter is, however, more poorly soluble), less preferably by tragacanth (because it froths too strongly) and causes the effervescent components to undergo a slightly slowed-down "soft" reaction in the mouth without however seriously slowing down the dissolution in water— owing to its good solubility. This measure has a particularly advantageous effect in the case of citric acid but is expediently also used in the case of malic acid, tartaric acid, adipic acid and ascorbic acid.

Theoretically, rapidly soluble fillers could also be coated with hydrocolloid, but this is a technologically complicated step since the water introduced by the solution of the hydrocolloid into the mixture must be removed again by drying, and the type and amount of hydrocolloid are difficult to optimize with regard to the dissolution rate.

A mixture with the same ratios in which only the citric acid is completely replaced by malic acid gives completely analogous results.

EXAMPLE 3

Mixtures are prepared with 250 mg each of the effervescent base prepared according to Example 2 and 10 mg each of nifedipine per tablet and are compressed to give tablets, the type of filler (750 mg each) being varied: all tablets dissolve in 100 ml of fresh water at 16° C. with little or no residue and exhibit good to very good behaviour on direct oral intake as a chewable tablet.

| Filler (750 mg each) | Hardness | Dissolution time |
|---|---|---|
| a. Mannitol | 5.8 | 45" |
| b. Maltisorb ® (= hydrogenated maltitol) | 6.2 | 45" |
| c. Fructose | 6.1 | 125" |
| d. Xylitol | 6.0 | 60" |
| e. Lactose | 6.3 | 40" |
| f. Sucrose | 5.9 | 75" |
| g. Glucose | 5.9 | 105" |
| h. Sorbitol instant | 5.9 | 180" |

It can clearly be seen that the rapidly soluble fillers glucose, fructose and especially sorbitol dramatically prolong the dissolution time (for the reasons stated at the outset). The substances used had the following sieve analysis:

| % by weight Particle size (mm) | Mannitol | Malti-sorb ® | Lactose | Fructose | Sorbitol | Xylitol |
|---|---|---|---|---|---|---|
| >0.5 | | | | 2.5 | | |
| >0.4 | | | | 5.5 | 0.85 | 5.4 |
| >0.315 | | | | 4.3 | 9.0 | 33.2 |
| >0.2 | 2.3 | 2.8 | | 29.2 | 48.1 | 60.2 |
| >0.1 | 27.5 | 12.5 | 5.5 | 30.5 | 33.0 | 1.5 |
| >0.05 | 36.5 | 51.6 | 29.6 | 22.4 | 8.5 | |
| >0.05 | 33.7 | 32.7 | 64.5 | 5.6 | 1.0 | |

The more slowly soluble first three fillers can be used as fine particles without seriously prolonging the dissolution time; the more rapidly soluble last three fillers must be used in the form of coarser particles, sorbitol still being unsatisfactory with a dissolution time of three minutes, as can be seen.

EXAMPLE 4

Mixtures are prepared analogously to Example 3, except that—for different active substances—the fillers are varied in type and amount depending on the active substance and are made up with the effervescent base to 1000 mg per tablet in each case. All mixtures were compressed to give tablets having a hardness of 4.5–6.0; they dissolve in 100 ml of fresh water (15°–20° C.) with little or no residue (with the exception of any suspended particles or slight turbidity in the case of insoluble or poorly soluble active substances) and exhibit good to very good behaviour on direct oral intake as a chewable tablet:

| Active substance (mg) | Filler(s) (mg) | Effervescent base (mg) | $t_{diss}$ (sec) |
|---|---|---|---|
| a) 100 acetyl-salicylic acid (corresponding to Example 2) | 700 mannitol 110 (flavour, sweeteners, PVP, etc.) | 190 | 55 |
| b) 10 nifedipine | 720 mannitol 40 (flavour, sweeteners, PVF, etc.) | 240 | 50 |
| c) 100 Allopurinol | 500 xylitol 20 (flavour, sweeteners, PVP, etc.) | 480 | 75 |
| d) 40 Furosemide | 720 mannitol, 10 PVP | 240 | 100 |
| e) 10 cisapride | 740 mannitol 20 (flavour, sweeteners, PVP, etc.) | 240 | 60 |
| f) 10 loratadine | 90 lactose 540 mannitol 110 (flavour, sweeteners, PVP, etc.) | 260 | 90 |
| g) 45 multivitamin mixture | 440 xylitol 390 mannitol 20 (flavour, sweeteners, PVP, etc.) | 150 | 60 |

EXAMPLE 5

A mixture of different fillers is often desired for reasons relating to taste. Example 3 was repeated, different filler mixtures being used. Under certain circumstances, such mixtures also permit the use of more rapidly soluble fillers, at least in part:

| | | |
|---|---|---|
| a. Mannitol (500 mg)/ sorbitol (250 mg) | 4.0 | 70" |
| b. Mannitol (500 mg)/ fructose (250 mg) | 4.0 | 75" |
| c. Xylitol (375 mg)/ lactose (375 mg) | 4.5 | 45" |
| d. Xylitol (375 mg)/ lactose (225 mg) | 4.0 | 45" |
| e. Fructose (375 mg)/ lactose (375 mg) | 4.5 | 55" |
| f. Fructose (600 mg)/ lactose (150 mg) | 4.5 | 95" |
| g. Glucose (375 mg)/ lactose (375 mg) | 5.5 | 70" |
| h. Glucose (600 mg)/ lactose (150 mg) | 4.5 | 95" |

EXAMPLE 6

The mixture of Example 4 g) is repeated, except that only mannitol is used as the filler, but in changing amounts or ratios to the effervescent base. It is found that both the dissolution time in the water and the action as a chewable tablet in the mouth can be classed as good to very good at effervescent base: mannitol ratios=15:85 to 30:70. At a ratio of 35–40:65–60, on the other hand, the dissolution time is of course gratifyingly low but the effervescent action in the mouth is already found to be too strong or the taste too acidic:

| Effervescent base | Filler | Chewable tablet | Hardness | Dissolution time |
|---|---|---|---|---|
| (parts by weight) | | | | |
| 15 | 85 mannitol | very good | 5.0 | 55" |
| 20 | 80 mannitol | very good | 5.5 | 55" |
| 25 | 75 mannitol | good | 5.5 | 45" |
| 30 | 70 mannitol | good | 5.0 | 40" |
| 35 | 65 mannitol | initially acidic | 5.5 | 35" |
| 40 | 60 mannitol | too acidic | 5.0 | 35" |

EXAMPLE 7

The mixtures of Example 5 g) and 5 h) were repeated, with further variation of the mixing ratio between glucose and lactose on the one hand and the hardness of the compressed tablets on the other hand; as can be seen, a still acceptable dissolution time is obtained even at relatively great tablet hardness; these tablets, too, were readily or very readily chewable or suckable on direct oral intake:

| Filler (mg) | Hardness (kp) | Dissolution time (s) | Residue |
|---|---|---|---|
| Glucose 750 | 5.9 | 105 | none |
| Glucose 562 Lactose 188 | 5.9 | 70 | none |
| Glucose 375 Lactose 375 | 6.3 | 70 | trace |
| Glucose 188 Lactose 562 | 6.4 | 65 | trace |
| Lactose 750 | 6.3 | 40 | slight |

EXAMPLE 8 (negative example)

Sorbitol alone is so rapidly soluble, in particular coarse-particled sorbitol instant, which however is porous owing to the spray drying, that—as already mentioned—tablets produced with sorbitol alone as filler have an undesirably long dissolution time, this being dependent on the particle size:

| Filler (mg) | Hardness (kp) | Dissolution time (s) | Residue |
|---|---|---|---|
| Sorbitol instant | 6.5 | 150 | none |
| Sorbitol P300 | 6.5 | 150 | none |
| Sorbitol 60W (crystalline) | 6.5 | 160 | none |

EXAMPLE 9

468 g of citric acid powder, 312 g of fine citric acid granules and 150 g of sodium cyclamate are introduced into a heatable vessel and heated to 60° C. with stirring. At 60° C., 420 g of sodium bicarbonate are added. The mass is heated to 60° C. again with stirring.

In addition, 90 ml of a solution of 60 g of maltodextrin, 12 g of trisodium citrate dihydrate and 59 g of water are prepared. 9 ml of this solution are now sucked in and allowed to react; 19 g of sodium carbonate are then added at 100 mbar and drying is carried out with slow stirring to 20 mbar. After drying, heating is carried out again to 60° C. and a second granulation is effected with 9 ml of the solution. The mass is dried to 100 mbar with slow stirring, whereupon a further 77 g of sodium carbonate are added. The product is then dried to 15 mbar and sieved to 1.6 mm. This effervescent base is then mixed with 2784 g of mannitol, 600 g of xylitol, 1200 g of lactose, 120 g of flavour and 135 g of isosorbide 5-mononitrate (90% lactose trituration) and compressed to give tablets of 1.05 g each.

EXAMPLE 10

The procedure is analogous to that of Example 2, except that tartaric acid is used instead of citric acid and, instead of acetylsalicylic acid, a standard multivitamin mixture, such as, for example, 50% of the RDA (=Recommended Daily Allowance) according to US standard, of vitamin E acetate (tocopheryl acetate), thiamine mononitrate, pyridoxine HCl, riboflavin phosphate sodium, nicotinamide, folic acid, biotin, calcium pantothenate, vitamin D3 100CWS, vitamin B12 0.1% and vitamin A palmitate CWS, so that the prepared tablet has the following composition (in mg):

| | |
|---|---|
| Tartaric acid powder | 86.00 |
| Malic acid | 8.30 |
| Sodium bicarbonate | 95.00 |
| Anhydrous sodium carbonate | 13.80 |
| Sodium cyclamate | 5.50 |
| Saccharin sodium | 1.10 |
| Aspartame | 0.30 |
| Trisodium citrate dihydrate | 0.95 |
| Maltodextrin | 1.00 |
| Mannitol | 700.00 |
| Multivitamin mixture | 45.50 |
| Flavour | 20.00 |
| | 977.45 |

The tablet exhibits satisfactory behaviour in the mouth and dissolves in a glass of water in less than 60 sec.

The invention can be used with many active substances, the dose of which may be up to about 200 mg. Active substances whose dose is only up to 100 mg are particularly advantageous since a small tablet is more suitable than a larger one for sucking or chewing.

What is claimed is:

1. A chewable tablet with an effervescent action and a tablet weight of less than 3 g, containing at least one pharmaceutically active substance, 15 to 50 percent by weight of an effervescent base comprising a solid, edible, organic acid and an alkali metal and/or alkaline earth metal carbonate and/or bicarbonate and 30 to 85% by weight of at least one soluble filler, characterized in that the acid particles and/or the carbonate particles of the effervescent base are coated with a hydrocolloid.

2. A chewable tablet with an effervescent action and a tablet weight of less than 3 g, containing at least one pharmaceutically active substance, 15 to 50% by weight of an effervescent base comprising a solid, edible, organic acid and an alkali metal and/or alkaline earth metal carbonate and/or bicarbonate and 30 to 85% by weight of a soluble filler, characterized in that the active substance is free of encapsulating substances and/or the tablet mixture is free of lubricants.

3. The chewable tablet according to claim 1, characterized in that the effervescent components are coated with 0.5 to 3.0 percent by weight of the hydrocolloid.

4. The chewable tablet according to claim 1, characterized in that the filler contains at least one of the following compounds: mannitol, hydrogenated maltitol, fructose, xylitol, lactose, sucrose, glucose.

5. The chewable tablet according to claim 1, characterized in that the filler combination is tailored so that the tablet— with the exception of any insoluble or slightly soluble active substances—dissolves in 100 ml of water at 15° to 20° C. in less than 120, seconds.

6. The chewable tablet according to claim 1, wherein said at least one soluble filler comprises a first soluble filler and a second soluble filler, 40 to 100% by weight of said first soluble filler has a particle size of more than 0.2 mm, while 60 to 95% by weight of said second soluble filler has a particle size of less than 0.1 mm, and wherein said first soluble filler is more rapidly soluble than said second soluble filler.

7. The chewable tablet according to claim 1, characterized in that the tablet weight is 600 to 1500 mg.

8. The chewable tablet according to claim 1, characterized in that the amount of the effervescent base in a tablet is 100 to 600 mg.

9. The chewable tablet according to claim 1, characterized in that at most half the amount of filler is replaced by sorbitol.

10. The chewable tablet according to claim 1, characterized in that a part of the acid is replaced by a second, solid, edible, organic acid differing from it.

11. The chewable tablet according to claim 1, characterized in that it contains 55 to 75% by weight of at least one filler, 15 to 25% by weight of an effervescent base and 15 to 25% by weight of isosorbide 5-mononitrate and/or isosorbide 5-dinitrate.

12. A process for the preparation of a chewable tablet according to claim 1, characterized in that the effervescent components are wet at an elevated temperature with a solution containing at least one hydrocolloid and are dried again, whereupon the effervescent base thus prepared is mixed with active substances and/or excipients and compressed to give tablets.

13. The process according to claim 12, characterized in that, before the drying and after the final cycle, 0.2 to 1, percent by weight of hydrocolloid in powder form is applied.

14. The chewable tablet according to claim 1, wherein said hydrocolloid is a freely or very soluble one.

15. The chewable tablet according to claim 3, wherein the effervescent components are coated with 1.0 to 2.0 percent by weight of said hydrocolloid.

16. The chewable tablet according to claim 3, wherein said hydrocolloid is at least one substance selected from the group consisting of maltodextrin, polyvinylpyrrolidone, and guar gum.

17. The chewable tablet according to claim 5, wherein the tablet dissolves in 90 sec at most.

18. The chewable tablet according to claim 6, wherein the first soluble filler is selected from the group consisting of fructose, xylitol, or sorbitol, and the second soluble filler is selected from the group consisting of mannitol, hydrogenated maltose, and lactose.

19. The chewable tablet according to claim 7, wherein the tablet weight is 700 to 1200 mg.

20. The chewable tablet according to claim 8, wherein the amount of the effervescent base in the tablet is 150 to 350 mg.

21. The chewable tablet according to claim 10, wherein about 5 to about 20 percent by weight of said acid is replaced by said second acid.

22. The process according to claim 12, wherein the step of wetting with said solution and drying is repeated between one to five times.

23. The process according to claim 12, characterized in that, before the drying and after the final cycle 0.4 to 0.6 percent by weight of hydrocolloid in powder form is applied.

24. The chewable tablet according to claim 10, wherein the second organic acid is malic acid.

* * * * *